United States Patent
Fujii et al.

(10) Patent No.: US 6,486,161 B1
(45) Date of Patent: Nov. 26, 2002

(54) USE OF RIFAMYCIN DERIVATIVE FOR TREATING MASTITIS IN A DOMESTIC ANIMAL

(75) Inventors: Kenji Fujii, Akashi; Katsuji Yamashita, Kobe; Kazunori Hosoe, Takasago, all of (JP); Robert J. Yancey, Jr., Salem, CT (US); Jeffrey L. Watts, Portage, MI (US)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/463,580

(22) PCT Filed: Jul. 29, 1998

(86) PCT No.: PCT/US98/15308

§ 371 (c)(1),
(2), (4) Date: May 23, 2000

(87) PCT Pub. No.: WO99/06047

PCT Pub. Date: Feb. 11, 1999

(51) Int. Cl.$^7$ .................................................. A61K 31/50
(52) U.S. Cl. .................................................. 514/252.13
(58) Field of Search ..................................... 514/252.13

(56) References Cited

FOREIGN PATENT DOCUMENTS

| EP | 0 190 709 A | | 8/1986 |
| EP | 0190709 A | * | 8/1986 |
| EP | 0 366 914 A | | 5/1990 |
| FR | 2 248 024 A | | 5/1975 |

OTHER PUBLICATIONS

Yamane et al., "Synthesis and Biological Activity of 3'–Hydroxy–5'–Aminobenzoxazinorifamycin Derivatives", CHEMICAL AND PHARMACEUTICAL BULLETIN, vol. 41, No. 1, Jan. 1993, pp. 148–155, XP000197109.

K. Fujii et al., "In Vitro and in Vivo Antibacterial Activities of KRM–1648 and KRM–1657, New Rifamycin Derivatives", ANTIMICROBIAL AGENTS AND CHEMOTHERAPY, vol. 38, No. 5, 1994, pp. 1118–1122, XP002085087.

Craven et al., "Antibiotic Activity Against Intraleukocytic Staphlococcus Aureus in Vitro and in Experimental Mastitis in Mice", AMERICAN JOURNAL OF VETERINARY RESEARCH, vol. 44, No. 4, 1983, pp. 709–712, XP002085088.

Radaelli et al., "The use of Rifamycin SV in the Treatment of Bovine Mastitis", THE VETERINARY RECORD, vol. 88, No. 12, 1971, pp. 297–304, XP002085089.

* cited by examiner

Primary Examiner—Zohreh Fay
(74) Attorney, Agent, or Firm—Armstrong, Westerman & Hattori, LLP

(57) ABSTRACT

A method for treating mastitis in a domestic animal in need of such a treatment, which comprises administering to the animal a pharmaceutical composition comprising a rifamycin derivative of the formula (1):

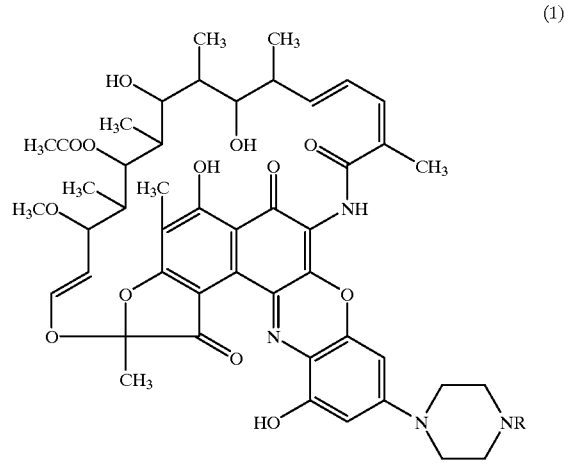

wherein R is an alkyl group having 1 to 7 carbon atoms or a physiologically acceptable salt thereof as an active ingredient, and a physiologically acceptable carrier. The present invention provides a novel therapeutic method effective for treatment of mastitis caused by bacterial infection in a domestic animal.

3 Claims, No Drawings

USE OF RIFAMYCIN DERIVATIVE FOR TREATING MASTITIS IN A DOMESTIC ANIMAL

This application is a 371 of PCT/US98/15308 filed on Jul. 29, 1998.

BACKGROUND OF THE INVENTION

The present invention relates to a method for treating mastitis in a domestic animal (mammal), a therapeutic medicament for, or use of certain rifamycin derivatives for the manufacture of a therapeutic medicament for mastitis in a domestic animal. More particularly, the invention relates to a method for treating an inflammatory disease caused by infection with a bacterium in the mammary gland of a domestic animal such as a dairy cow or a goat, which comprises administering to the animal a pharmaceutical composition comprising as an active ingredient a rifamycin derivative or a physiologically acceptable salt thereof, and a physiologically acceptable carrier. Also, the present invention provides a therapeutic medicament for mastitis in a domestic mammal which comprises said rifamycin derivative, or use of said derivative for the manufacture of said therapeutic medicament.

Mastitis in domestic animals raised for obtaining milk such as a dairy cow and a goat is a disease in which the mammary glands in the animals are infected with Staphylococcus (e.g., *Staphylococcus aureus*), *Escherichia coli*, or another pathogenic bacterium causing inflammation; or a disease related to such a bacterium. Mastitis is a very costly disease for the dairy industry due to its high incidence, and the resulting reduced milk production, reduced milk quality and increased culling (removal) of animals from dairy herds.

As described above, mastitis is a very serious disease in domestic animals, and a known therapy frequently used is the administration by infusion of an antimicrobial drug directly into the mammary gland of a domestic animal affected with mastitis. Most of the mastitis is cured or alleviated by such an infusion for treating mastitis. However, due to a change in the kind of bacterium causing mastitis and a lowering of susceptibility of a bacterium causing mastitis to existing antimicrobial drugs for treating mastitis, at present mastitis for which no therapeutic effect is obtained by known drugs has increased.

For instance, cefazolin which is a first-generation cephalosporin antibiotic has been used for treating this disease. However, cases wherein treatment of mastitis is difficult have increased because bacteria resistant to this antibiotic have appeared and increased at present. Also, although cefem antibiotics and the like have been used, their effect is not sufficient for treating mastitis. In order to develop more effective therapy, it is necessary to introduce a new, more effective therapeutic agent.

An object of the present invention is to provide a method for treating mastitis in a domestic animal in need of such a treatment, which comprises administering to the animal a pharmaceutical composition comprising a rifamycin derivative of the formula (1):

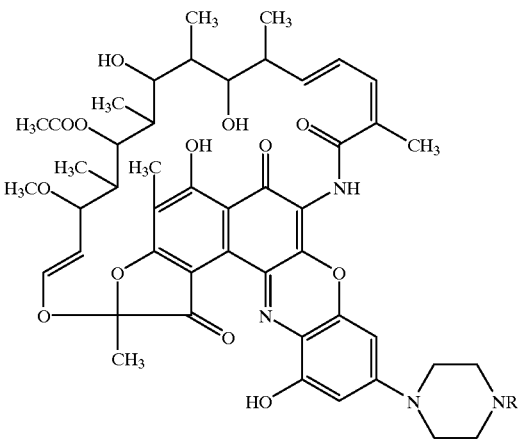

wherein R is an alkyl group having 1 to 7 carbon atoms or a physiologically acceptable salt thereof as an active ingredient, and a physiologically acceptable carrier. Also, the present invention provides a therapeutic medicament for mastitis in a domestic mammal which comprises said rifamycin derivative, or use of said derivative for the manufacture of said therapeutic medicament.

This and other objects of the present invention will become apparent from the following description.

SUMMARY OF THE INVENTION

In accordance with the present invention, there is provided a method for treating mastitis in a domestic animal in need of such a treatment, which comprises administering to the animal a pharmaceutical composition comprising a rifamycin derivative of the formula (1):

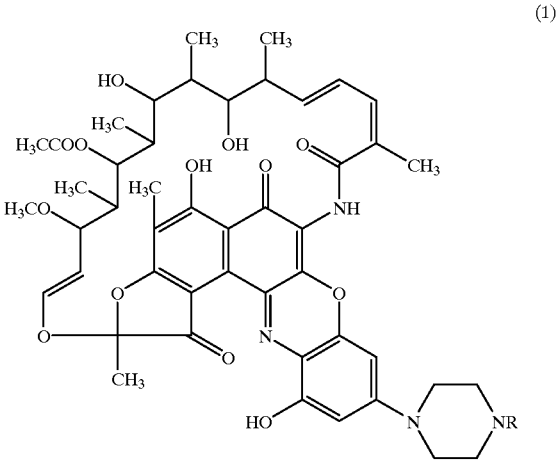

wherein R is an alkyl group having 1 to 7 carbon atoms or a physiologically acceptable salt thereof as an active ingredient, and a physiologically acceptable carrier. Also the present invention provides a therapeutic medicament for mastitis in a domestic mammal comprising said rifamycin derivative or use of said derivative for the manufacture of said therapeutic medicament.

DETAILED DESCRIPTION

The alkyl group having 1 to 7 carbon atoms in R in the rifamycin derivative (1) used in the present invention includes linear, branched and cyclic alkyl groups such as methyl group, ethyl group, propyl group, isopropyl group, cyclopropyl group, butyl group, isobutyl group, sec-butyl group, tert-butyl group, cyclobutyl group, cyclopropylmethyl group, pentyl group, isopentyl group, sec-pentyl group, tert-pentyl group, 1,2-dimethylpropyl group, 1-ethylpropyl group, cyclopentyl group, cyclobutylmethyl group, hexyl group, 4-methylpentyl group, cyclohexyl group, 3-methylcyclopentyl group, heptyl group, isoheptyl group, and the like. Methyl, ethyl, propyl, isopropyl, cyclopropyl and isobutyl groups are preferred.

The rifamycin derivative (1) used in the present invention for treating mastitis in a domestic animal can be obtained by methods disclosed in, for example, Japanese Examined Patent Publication (Kokoku) No. 57275/1993, Japanese Unexamined Patent Publication (Kokai) Nos. 007291/1991, 101681/1991 and 03589/1992, and Chem. Pharm. Bull., Vol. 41, 148 (1993), and the like.

The rifamycin derivative (1) is able to form a salt with either an acid or a base. As the acid or base which can be used for the salt formation, any one capable of forming a salt with the rifamycin derivative (1) can be used. Examples of the salt with a base are (1) metal salts, particularly alkali metal salts such as sodium salts and potassium salts and alkaline earth metal salts such as calcium salts, (2) ammonium salts, and (3) amine salts, particularly salts with methylamine, ethylamine, diethylamine, triethylamine, pyrrolidine, morpholine and hexamethyleneimine, and the like. Examples of the salt with an acid are (1) salts with mineral acids such as sulfuric acid and hydrochloric acid, and (2) salts with organic acids such as p-toluenesulfonic acid, trifluoroacetic acid and acetic acid.

A physiologically acceptable salt of the rifamycin derivative (1) which can be used in the present invention is selected from the above-mentioned salts which are physiologically acceptable.

The domestic animal to be treated in the present invention is preferably an animal kept and/or fed for obtaining milk, such as a dairy cow or a goat.

Each of the rifamycin derivatives (1) wherein each R is methyl group, ethyl group, propyl group, isopropyl group, cyclopropyl group or isobutyl group was orally administered to mice in a dose of 1,000 mg/kg. They did not show any toxicity, so it was confirmed that the rifamycin derivatives shown by the formula (1) have low toxicity.

The pharmaceutical composition used according to the present invention is administered orally or parenterally. In case of parenteral administration of the above-mentioned composition to a domestic animal in need of treatment for mastitis according to the present invention, the composition may be injected or infused hypodermically, intradermally, intramuscularly or through the lactiferous duct in the form of an injection preparation or an infusion preparation. However, the administration route is not limited to these examples.

The pharmaceutical composition which contains as an active ingredient the rifamycin derivative (1), or its physiologically acceptable salt, used according to the present invention may be, for example, in the form of an injection preparation or an infusion preparation such as an aqueous suspension preparation, an oily suspension preparation, an emulsion preparation or a solution preparation. The above-mentioned composition used according to the present invention may also be, for example, in the form of a preparation for oral administration such as powder, tablets including sugar-coated tablets, capsules, pills, fine granules, granules or syrup. A physiologically acceptable carrier contained in the pharmaceutical composition used in the present invention may be any carrier including a solvent which is usually used for preparing a pharmaceutical composition in the art. A solvent used in the injection or infusion preparation according to the present invention includes water, a water-miscible solvent and an oily solvent. Examples of the water-miscible solvent are ethanol, benzyl alcohol, propylene glycol, polyethylene glycol, glycerol and other solvents miscible with water in any preparation. Preferably ethanol and benzyl alcohol, and more preferably benzyl alcohol is used. As the oily solvent, any one in liquid form at ordinary temperatures, such as a vegetable oil or a fatty acid ester, can be used. Examples of the vegetable oil are purified olive oil, peanut oil, sesame oil, camellia oil, and the like. However, the solvent is not limited thereto.

To the suspension preparations may be added a surfactant such as a polysorbate. In order to prepare an emulsion preparation, a surfactant such as a sorbitan fatty acid ester, benzalkonium chloride or polyoxyethylene hydrogenated castor oil may be used. Also, the carriers used for preparing the pharmaceutical composition used according to the present invention include organic or inorganic, solid or liquid, usually inactive pharmaceutical carriers suitable for oral administration. Examples of the carrier are crystalline cellulose, gelatin, lactose, starch, magnesium stearate, talc, vegetable and animal oils and fats, gums, polyalkylene glycols, and the like. However, the carrier is not limited thereto. The amount of the active ingredient (effective component) in the pharmaceutical composition used according to the present invention in the preparations can be varied within the range of 0.2 to 50% by weight based on the carrier. The pharmaceutical composition used in the present invention may contain one or more other therapeutic agent for treating mastitis in a domestic animal and/or other medicaments, which are compatible therewith. In that case, needless to say, the rifamycin derivative (1) or its physiologically acceptable salt does not have to be the main ingredient in the preparations.

The pharmaceutical composition used in the present invention is generally administered in such a dosage as to achieve the desired actions, i.e. in an effective amount without any side effect.

A concrete dosage of the composition used according to the present invention should be determined by a veterinarian. In an infusion preparation to be administered through the lactiferous duct or an injection preparation to be administered to a mammary gland or a vein, however, an amount in the range of about 1 mg–about 10 g, preferably in the range of about 5 mg–about 5 g, on the basis of the rifamycin derivative (1) may be usually administered per day per mammary gland of a cow.

In an oral preparation, an amount in the range of about 500 mg–about 50 g, preferably in the range of about 1 g–about 30 g, on the basis of the rifamycin derivative (1) may be usually administered per day per cow. The pharmaceutical composition used in the present invention may be administered as a pharmaceutical preparation which contains 1 mg–50 g, preferably 2 mg–10 g, on the basis of the rifamycin derivative (1) in a dosage unit.

The present invention is more specifically described and explained by means of the following Examples and Preparation Examples, but it is to be understood that the present invention is not limited to these examples.

In the following examples, the rifamycin derivatives (1) were prepared according to U.S. Pat. No. 4,983,602 and rifampin was obtained from Sigma Chemical Company.

EXAMPLE 1

The therapeutic effect of the rifamycin derivative (1) was determined in the following in vivo tests for *S. aureus*-induced murine mastitis.

Lactating multiparous female Carworth CF1 mice, weighing approximately 40 g and 4 to 8 days after parturition, were used for mastitis model. These mice were anesthetized with ether and were infected with an 0.1 ml aliquot containing $2\times10^4$ colony forming unit (CFU) of *S. aureus* 6097 via the test duct. Rifamycin derivatives (0.1 ml) were administered by the same route at 1 hour after infection. At 6 days after infection, each infected gland was cultured for the presence of bacteria. Measurement of the effectiveness of the compound was calculated at that time and was reported as $ED_{50}$ (Mastitis) or $ED_{50}$ (Culture). The $ED_{50}$ (Mastitis) was the amount of compound in milligrams per kilogram of body weight per day at which 50% of the infected mice did not develop mastitis in the infected gland. Mastitis was defined as any abnormality in the challenge-exposed gland including swelling, redness, necrosis, or nodules (abscesses) evident by visual observation or palpation. The $ED_{50}$ (Culture) was the amount of compound in milligrams per kilogram of body weight per day at which 50% of the mice had no bacteria cultured from the inoculated gland. The $ED_{50}$ values were calculated by probit analysis. In these mice at the challenge-exposure dose of $2\times10^4$ CFU, 90% to 100% of the mice were mastitic and/or culture-positive at 6 days after infection. The results are shown in Table 1, wherein R is the alkyl group R in the rifamycin derivative (1).

TABLE 1

Dose titrations against *Staphylococcus aureus* 6097 in the mouse mastitis model.

| Compound | Route | ED (mg/kg/d) Mastitis | ED (mg/kg/d) Culture |
|---|---|---|---|
| R = methyl | IMM | 0.3 | 0.3 |
|  | SC | 0.2 | 0.5 |
| R = propyl | IMM | 0.2 | 0.2 |
|  | SC | 0.3 | 0.4 |
| R = ethyl | IMM | 0.3 | 0.4 |
|  | SC | 0.4 | 1.5 |
| R = isopropyl | IMM | 0.2 | 0.2 |
|  | SC | 0.4 | 0.6 |
| R = isobutyl | IMM | 0.3 | 0.3 |
|  | SC | 3.5 | 3.5 |
| Rifampin | IMM | 0.4 | >2.0 |

IMM = intramammary
SC = subcutaneous

The rifamycin derivative (1) showed superior activity compared to rifampin in the prevention of onset and the inhibition of growth (or the killing) of tested strains.

EXAMPLE 2

The therapeutic effect of the rifamycin derivative (1) was determined by *S. aureus* intracellular killing assay in bovine polymorphonuclear neutrophil (PMN).

PMN (Polymorphonuclear Leukocyte) Isolation

The procedure for PMN isolation was as described in Carlton et al. (Proc. Soc. Exp. Biol. Med. 142: 853–858 (1973)).

Bovine blood collected by venipuncture in 50-ml syringes containing 1.5% EDTA (pH 6.8) was centrifuged at 1,000×g for 25 min. The plasma-buffer layer and the top few milliliters were discarded. The packed erythrocyte fraction was pooled in 0.8% NaCl-phosphate buffer (pH 6.8) and 10 ml was placed in 20 ml of sterile water for 40 seconds to lyse the erythrocytes. Immediately thereafter, 10 ml of a 2.7% NaCl-phosphate buffer solution was added to restore isotonicity. The leukocytes, consisting of $\leq$84% PMNs, were washed twice and suspended in HBSS. PMNs were adjusted to a final concentration of $10^7$ cells per ml.

Intracellular Killing

The intracellular killing assay was carried out as described in Sanchez et al. (Antimicrobial Agents and Chemotherapy 29(4): 634–638 (1986)).

Bovine blood PMNs and bacteria (1:1) were suspended in HBSS containing 10% heterologous bovine serum. The mixture was incubated for 90 minutes at 37° C. in Erlenmeyer flasks with rotational mixing at 110 rpm. Lysostaphin (5 μg/ml) was added to the mixture for the final 15 minutes of incubation. The infected PMNs were washed 3 times by low-speed centrifugation and suspended in HBSS. Cells were pipetted (1 ml) into each well of a six-well cluster dish (Bellco Glass, Inc., Vineland, N.J.) at $5\times10^6$ PMNs per well. PMNs were allowed to attach and form a monolayer for 10 minutes at 37° C. The supernatant fluid with unattached cells was discarded, and 2 ml of fresh HBSS was added to each well. The rifamycin derivatives to be tested were then added to the wells (one six-well plate per drug). These derivatives were dissolved in dimethylsulfoxide, and then diluted in HBSS to final solvent concentrations of 0.01% (vol/vol) or less.

After overnight incubation (18 to 21 hours) at 37° C. with 1% $CO_2$, lysostaphin (5 μg/ml) was added to each well for 15 min (at 37° C.) to kill extracellular bacteria. The monolayers were washed with HBSS, and the cells were lysed by addition of 1 ml of water to each well. The number of viable bacteria was then estimated by plate counts on brain heart infusion agar. The criteria for intracellular killing by a rifamycin derivative were that the bacteria count must be significantly reduced (at the 95% confidence limit) compared with untreated controls as determined by a one-tailed Student t test and that the compound must not be cytotoxic for PMNs as determined by the trypan blue exclusion technique. The results are shown in Table 2, wherein R is the alkyl group in the rifamycin derivative (1).

TABLE 2

Effect on the intracellular killing of *Staphylococcus aureus* 9203.

| Compound | MIC (μg/ml) | CFU/ml ISD ($\times 10^3$) (% reduction) 1X MIC | CFU/ml ISD ($\times 10^3$) (% reduction) 100X MIC |
|---|---|---|---|
| R = methyl | $\leq$0.03 | 0.3 ± 0.1 (92.0) | 0.0 (100) |
| R = propyl | $\leq$0.03 | 0.14 ± 0.08 (96.0) | 0.0 (100) |
| R = ethyl | $\leq$0.03 | 0.09 ± 0.04 (97.0) | 0.0 (100) |
| R = isopropyl | $\leq$0.03 | 0.0 (100) | 0.0 (100) |
| R = isobutyl | $\leq$0.03 | 0.15 ± 0.06 (95.0) | 0.0 (100) |
| Rifampin | $\leq$0.03 | 0.6 ± 0.3 (83.0) | 0.5 ± 0.2 (85.0) |
| Cloxacillin | —[1] | —[1] | 5.9 ± 1.9 (0.0) |
| none | —[1] | —[1] | 3.3 ± 0.9 |

[1]Not determined.

The rifamycin derivative (1) exhibited a higher killing activity than rifampin against tested strains existing in cells. The rifamycin derivative (1) lowered the number of colonies (92–100%) in the same concentration as MIC in vitro.

EXAMPLE 3

The therapeutic effect on mastitis in a domestic animal of the rifamycin derivative (1) used in the present invention was demonstrated by means of a therapeutic test wherein bovine mammary glands affected with mastitis were treated with the rifamycin derivative (1).

As the rifamycin derivative (1), a compound A wherein R is methyl group, i. e. R= $CH_3$, was examined for its therapeutic effect on bovine mastitis as follows.

The therapeutic test for infection in bovine mammary glands was carried out by inoculating 603 cells of Staphylococcus [*Staphylococcus aureus* B83-1 strain (derived from Newbould 305)] into one mammary gland of a Holstein dairy cow (2–5 years old) to cause experimental mastitis.

To one mammary gland of each cow in a treated group, the compound A used in the present invention was administered (infused through the lactiferous duct) in an amount of 50 mg in 10 ml of benzyl alcohol per day successively for two days, twenty-one days after the infection. To one mammary gland of each cow in a control group, benzyl alcohol was administered in an amount of 10 ml per day in the same manner as in the treated group. The therapeutic effect of the compound A was examined by counting colony forming units (CFUs) of Staphylococcus in 1 ml of milk obtained from a cow subjected to the test. Comparing the above two groups, the therapeutic effect of the compound A on bovine mastitis was evaluated.

Staphylococcus was inoculated into forty-four mammary glands of eleven cows. Twenty-one days later, the number of mammary glands wherein Staphylococcus was separated from milk, i.e. number of mammary glands with mastitis, was counted. This number was thirty-eight. Twenty-one of the infected mammary glands were used in the treated group to which the compound A was administered, and the other sixteen were used in the control group.

Seven days, fourteen days, twenty-one days and twenty-eight days after the administration, the drug efficacy was examined by separating Staphylococcus from milk obtained from the treated cow and counting the CFUs of the separated Staphylococcus. It was judged that a mammary gland wherein the CFUs decreased to at most ten cells per ml (negative) in all the examined days was successfully treated, that is to say, that the mammary gland with mastitis was cured.

In the treated group, fourteen mammary glands in twenty-two mammary glands to which the compound A was administered were negative in all the examined days from seven days after the administration of the compound A. It was judged that the treatment with the compound A succeeded in curing bovine mastitis. The ratio of success to failure, i.e. curing ratio, in this test was 64%. In sixteen mammary glands in the control (non-treated) group, at least eleven CFUs of Staphylococcus were found per ml of milk obtained therefrom in all the examined days. It was confirmed that spontaneous cures did not occur in the control group. As is clear from the results, it is found that bovine mastitis caused by Staphylococcus infection can be cured by administration of the rifamycin derivative (1), especially by administration of the compound used in the present example, with a high curing ratio.

EXAMPLE 4

The mutation frequency for development of resistance to the rifamycin derivative (1) as compared to rifampin was determined with selected *Staphylococcus aureus* strains.

Four *S. aureus* strains were used: *S. aureus* 30857, a rifampin-resistant isolate: *S. aureus* 6097, a strain used in the mouse mastitis test and originally from a case of gangrenous bovine mastitis; *S. aureus* B83-1, derived from the Newbould 305 strain; and *S. aureus* ATCC 29213, the in vitro control stain recommended by NCCLS.

All *S. aureus* strains were maintained on 3 mm glass beads immersed in trypticase soy broth (BBL Microbiology Systems, Cockeysville, Md.) with 10% glycerol and held at −70° C. until revived. Prior to testing, the strains were subcultured on tryptose blood agar base (Difco, Detroit, Mich.) supplemented with 5% sheep blood for 24 hours at 35° C.

These compounds were dissolved in 95% ethanol, a solution which was then diluted to 10% ethanol with sterile distilled water. Further dilutions were conducted in water.

MIC (Minimum Inhibitory Concentration) determinations were performed using the microbroth dilution method. (National Committee for Clinical Laboratory Standards, 1990 Approved Standard M7-A8. Methods for dilution antimicrobial susceptibility tests for bacteria that grow aerobically, 3rd edition. National Committee for Clinical Laboratory Standards, Villanova, Pa.) The results are shown in Table 3, wherein R is the alkyl group R in the rifamycin derivative (1).

TABLE 3

Minimum inhibitory concentrations (MIC) with selected strains of *Staphylococcus aureus*

| Strain No. | MIC ($\mu$g/ml) | | |
|---|---|---|---|
| | R = methyl | R = isobutyl | Rifampin |
| 30857 | 0.5 | >4.0 | >4.0 |
| 6097 | 0.000061 | 0.00098 | 0.0019 |
| B83-1 | 0.000061 | 0.0019 | 0.0019 |
| ATCC 29213 | 0.000061 | 0.0019 | 0.0019 |

The rifamycin derivative (1) was as effective as rifampin. In particular, the compound wherein R is methyl had a very low MIC and was effective against rifampin-resistant strains.

The mutation frequency for development of resistance to the compounds tested was determined by the following method. A single colony of each strain was removed from the surface of a blood agar plate with a cotton swab, suspended in 5 ml of Mueller-Hinton broth (BBL), and streaked on the entire surface of five Mueller-Hinton agar plates. The plates were incubated overnight under aerobic conditions at 35° C., growth was removed from the agar using a sterile cotton swab, and the bacteria were suspended in 10 ml physiological saline. This bacterial suspension was the inoculum for the mutation frequency determinations. Standard plate counts were performed on the inoculum by performing serial dilutions and plating a 0.1 ml aliquot on the surface of ten Mueller-Hinton agar plates at each concentration. The plates were incubated for 18–24 hours at 35° C. under aerobic conditions and colony counts performed. Mean bacterial counts were calculated for the inoculum with each strain.

A 0.1 ml aliquot of the inoculum was then used to inoculate the entire surface of ten plates each containing 1, 10, and 100 $\mu$g/ml of the test antimicrobial agents. The plates were incubated for 18–24 hours at 35° C. under aerobic conditions and colony counts performed. Mean bacterial counts were calculated for each antimicrobial concentration and the mutation frequency calculated by dividing the number of colonies which grew on the drug containing media by the inoculum size. The results are shown in Table 4, wherein R is the alkyl group R in the rifamycin derivative (1).

TABLE 4

Mutation frequency for resistance with selected strains of S. aureus

| Strain No. | Inoculum | Compound | Mutation frequency at the indicated concentrations ($\mu$g/ml) | | |
|---|---|---|---|---|---|
| | | | 1 | 10 | 100 |
| 30857 | 6.4 × 10$^{10}$ | Rifampin | >1.0 × 10$^{-7}$ | >1.0 × 10$^{-7}$ | >1.0 × 10$^{-7}$ |
| | | R = isobutyl | >1.0 × 10$^{-7}$ | >1.0 × 10$^{-7}$ | >1.0 × 10$^{-7}$ |
| | | R = methyl | <1.6 × 10$^{-10}$ | <1.6 × 10$^{-10}$ | <1.6 × 10$^{-10}$ |
| 6097 | 5.5 × 10$^{10}$ | Rifampin | 1.2 × 10$^{-8}$ | 2.0 × 10$^{-8}$ | 4.9 × 10$^{-9}$ |
| | | R = isobutyl | 9.5 × 10$^{-8}$ | 8.9 × 10$^{-8}$ | 9.9 × 10$^{-8}$ |
| | | R = methyl | 4.0 × 10$^{-8}$ | <1.8 × 10$^{-10}$ | <1.8 × 10$^{-10}$ |
| B83-1 | 5.7 × 10$^{9}$ | Rifampin | 3.7 × 10$^{-8}$ | 4.5 × 10$^{-8}$ | 1.9 × 10$^{-8}$ |
| | | R = isobutyl | 5.0 × 10$^{-8}$ | 5.2 × 10$^{-8}$ | 4.7 × 10$^{-8}$ |
| | | R = methyl | 1.5 × 10$^{-8}$ | <1.8 × 10$^{-9}$ | <1.8 × 10$^{-9}$ |
| ATCC 29213 | 8.7 × 10$^{8}$ | Rifampin | 2.6 × 10$^{-8}$ | 2.5 × 10$^{-8}$ | 1.9 × 10$^{-8}$ |
| | | R = isobutyl | 3.0 × 10$^{-8}$ | 3.7 × 10$^{-8}$ | 3.5 × 10$^{-8}$ |
| | | R = methyl | 2.1 × 10$^{-9}$ | <1.1 × 10$^{-9}$ | <1.1 × 10$^{-9}$ |

The mutation frequency for resistance observed in vitro to the rifamycin derivative (1) is almost equal to, or much less than, that of rifampin.

EXAMPLE 5

The antibacterial effect of the rifamycin derivative (1) against rifampin-resistant *Staphylococcus aureus* bacterial strains was determined. The tested bacterial strains were isolated from a variety of animal diseases as well as laboratory strains.

All bacteria were maintained on 3 mm glass beads immersed in trypticase soy broth (BBL Microbiology Systems, Cockeysville, Md.) with 10% glycerol and held at −70° C. until revived. Prior to testing, the organisms were subcultured on tryptose blood agar base (Difco, Detroit, Mich.) supplemented with 5% sheep blood for 24 hours at 35° C.

The compounds were dissolved in 95% ethanol and diluted to 10% ethanol in sterile, distilled water except for the compounds used in the in vivo testing where saline was used to dilute the original ethanol/drug suspension. Further dilutions were conducted in water or saline.

MICs were determined using the microbroth dilution method. In addition to the test organisms, the following quality control strain also was tested: *Staphylococcus aureus* ATCC 29213. The results are shown in Table 5, wherein R is the alkyl group R in the rifamycin derivative (1).

TABLE 5

Minimum inhibitory concentration (MIC) against rifampin-resistant S. aureus isolated from diseased animals.

| | MIC ($\mu$g/ml) | |
|---|---|---|
| Strain No. | Rifampin | R = methyl |
| 30869 | 4.0 | 0.25 |
| 12637 | >32.0 | 0.25 |
| 30858 | 8.0 | 2.0 |
| 30867 | 32.0 | 0.5 |
| 30859 | >32.0 | 0.25 |

TABLE 5-continued

Minimum inhibitory concentration (MIC) against rifampin-resistant S. aureus isolated from diseased animals.

| | MIC ($\mu$g/ml) | |
|---|---|---|
| Strain No. | Rifampin | R = methyl |
| 30860 | >32.0 | 4.0 |
| 30865 | 32.0 | 0.06 |
| 30863 | >32.0 | 0.25 |
| 30888 | >32.0 | 0.13 |
| 30871 | >32.0 | 2.0 |
| 31068 | 4.0 | 2.0 |
| 30862 | >32.0 | 2.0 |
| B93-728M | 2.0 | 0.5 |
| Range | 2.0–>32.0 | 0.06–4.0 |

The rifamycin derivative (1) exhibits antibacterial activity against almost all rifampin-resistant isolates, and no cross resistance was observed.

Preparation Example 1

In 800 g of a purified sesame oil was suspended 200 g of the compound A (the rifamycin derivative (1) wherein R is CH$_3$) which was aseptically prepared and pulverized into fine powder. Brown ampoules were charged with the thus obtained suspension in an amount of 2 g per ampoule. The ampoules were sealed to give oily suspension injection preparations containing 200 mg of the compound A per gram of the suspension.

Preparation Example 2

In 800 g of a purified olive oil was suspended 200 g of the compound A which was aseptically prepared and pulverized into fine powder. Brown ampoules were charged with the thus obtained suspension in an amount of 2 g per ampoule. The ampoules were sealed to give oily suspension injection preparations containing 200 mg of the compound A per gram of the suspension.

Preparation Example 3

A mixture of 100 g of the compound A, 55 g of lactose and 45 g of dried potato starch was kneaded with 20 ml of water, and was granulated by extruding through a 16 mesh screen and drying at 40° C. to give granules containing 50 g of the compound A per 100 g of granules.

In addition to the ingredients used in the Examples, other ingredients can be used in the Examples as set forth in the specification to obtain substantially the same results.

What is claimed is:

1. A method for treating mastitis in a domestic animal in need of such a treatment, which comprises administering to the animal a pharmaceutical composition comprising a rifamycin derivative of the formula (1):

(1) 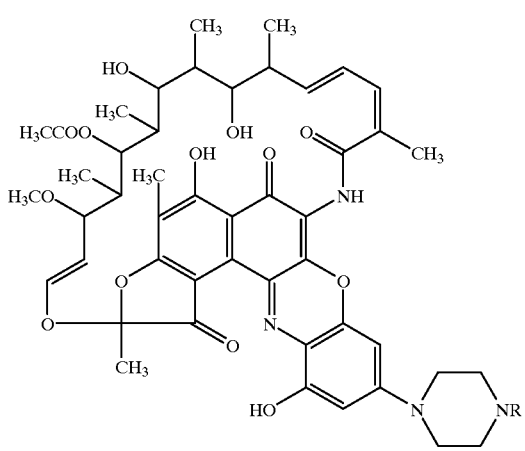
wherein R is an alkyl group having 1 to 7 carbon atoms or a physiologically acceptable salt thereof as an active ingredient, and a physiologically acceptable carrier.
2. The method of claim 1, wherein R is an alkyl group having 1 to 4 carbon atoms in said rifamycin derivative (1).
3. The method of claim 1, wherein R is methyl group in said rifamycin derivative (1).
* * * * *